United States Patent [19]

Nakao et al.

[11] Patent Number: 4,791,059
[45] Date of Patent: Dec. 13, 1988

[54] PROCESS FOR PREPARING LIPASE

[75] Inventors: Masahiro Nakao; Sumio Asami; Takaharu Tanaka; Kyoichi Ogura; Teruo Amachi; Hajime Yoshizumi; Hiroshi Ishigooka, all of Osaka, Japan

[73] Assignee: Suntory Limited, Osaka, Japan

[21] Appl. No.: 844,389

[22] PCT Filed: Jul. 19, 1985

[86] PCT No.: PCT/JP85/00409
§ 371 Date: Mar. 17, 1986
§ 102(e) Date: Mar. 17, 1986

[87] PCT Pub. No.: WO86/00925
PCT Pub. Date: Feb. 13, 1986

[30] Foreign Application Priority Data

Jul. 20, 1984 [JP] Japan .................. 59-149585

[51] Int. Cl.$^4$ .............................. C12N 9/20
[52] U.S. Cl. ...................... 435/198; 435/882
[58] Field of Search .............. 435/198, 882

[56] References Cited

U.S. PATENT DOCUMENTS 4,565,698 1/1986 Yoshizumi et al. ............ 424/93
4,670,255 6/1987 Yoshizumi et al. ............ 424/93

FOREIGN PATENT DOCUMENTS 55-42532 3/1980 Japan .
56-140887 11/1981 Japan .

OTHER PUBLICATIONS

Chemical Abstracts vol. 81, No. 15, p. 112, right column, No. 87058u.

Primary Examiner—Thomas G. Wiseman
Assistant Examiner—Charles L. Patterson, Jr.
Attorney, Agent, or Firm—Burns, Doane, Swecker & Mathis

[57] ABSTRACT

This invention relates to a process for preparation of a novel lipase. The process is characterized by culturing a microorganism belonging to Staphylococcus capitis and capable of producing lipase in a culture medium to accumulate lipase in the cultured broth and recovering the lipase from the broth. Since the pH of this lipase is in a slightly alkali region and the lipase substantially completely converts glyceride to fatty acids and glycerin, it is useful for the economic preparation of fatty acids by the hydrolysis of fats or oils.

2 Claims, 7 Drawing Sheets

PROCESS FOR PREPARING LIPASE

DESCRIPTION

1. Technical Field

The present invention is concerned with a process for preparing a novel lipase. More particularly, it relates to the process for preparing the novel lipase involving the use of strains of *Staphylococcus capitis*, which lipase provides free fatty acids and glycerin from triglyceride.

2. Background Art

For the preparation of lipase using microorganisms, particularly bacteria, the processes using bacteria belonging to the genera such as Pseudomonas, *Chromo bacterium*, Achromobacter, and Corynebacterium are known. However, when lipase derived from these microorganisms is used to hydrolyze fats or oils particularly triglycerides, substantial amounts of monoglycerides and diglycerides are formed in addition to fatty acids and glycerin. This is thought to arise from the recombination of fatty acids and glycerin by the action of lipase or from the termination of hydrolysis by lipase during the monoglyceride-forming stage or the diglyceride-forming stage. Accordingly, the process for preparing fatty acids using such a known lipase by the hydrolysis of fats or oils has both technical and economical disadvantages.

DISCLOSURE OF THE INVENTION

Accordingly, the present invention provides a lipase for use in the preparation on an industrial scale of fatty acids by the enzymatic hydrolysis of fats or oils in which triglyceride is hydrolyzed so completely that fatty acids and glycerin are formed but virtually no monoglyceride and diglyceride are formed.

The present inventors found that such lipase is produced by *Staphylococcus capitis*, and they subsequently isolated and purified the same in a pure form.

Consequently, this invention provides a process for preparing a novel lipase characterized by the steps of: culturing a microorganism belonging to *Staphylococcus capitis* and capable of producing the novel lipase in a culture medium to accumulate the lipase in the fermentation broth and recovering the lipase from the broth. This lipase hydrolyzes triglyceride virtually completely to fatty acids and glycerin so that no monoglyceride and diglyceride are produced.

THE BEST MODE FOR CARRYING OUT THE INVENTION

Lipase-producing Microorganisms

Figure 1:
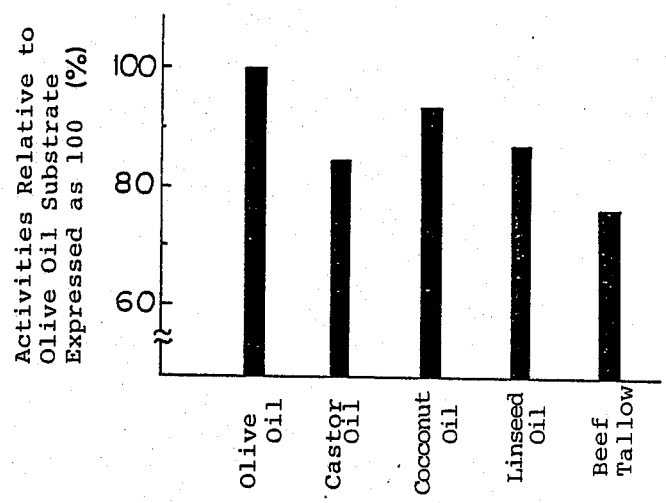
FIG. 1 shows the activities of the lipase of the present invention for different substrates relative to its activity for olive oil as a substrate, expressed as 100%.

The lipase-producing microorganisms used in the process of the present invention are of the species *Staphylococcus capitis* having the ability to produce lipase. Any bacteria having such a property may be used in the process of the invention. For example, strains of *Staphylococcus capitis* which are preserved at the American Type Culture Collection (12301 Parklawn Drive, Rockville, Maryland 20852, U.S.A.) and readily available therefrom may be used. Such strains of *Staphylococcus capitis* as ATCC 27840, ATCC 27841, ATCC 27842, and ATCC 27843 can be cited as examples thereof.

In addition, *Staphylococcus capitis* T-1-1(SAM0001), isolated for the first time from the human scalp by the inventors in the process of the invention, may be used. This strain possesses the following bacteriological characteristics:

(A) Morphology (1) Size: Cocci ranging in diameters from 0.8 $\mu$m ~ 1.2 $\mu$m and 2 to 4 cocci found in clusters.
(2) Motility: None.
(3) Sporulation: Not observed.
(4) Gram Stain: Positive.
(5) Acid-resistance: None.

(B) Growth Characteristics (1) Bouillon Agar Plate Culture: Colonies slightly convex, round, smooth surface, opaque white, and small in size with diameters ranging from 1 mm to 3 mm.
(2) Bouillon Liquid Culture: Good growth; broth entirely turbid.
(3) Bouillon Gelatin Stab Culture: Gelatin not liquefied; growth linear.
(4) Bouillon Agar Slant Culture: Colonies slightly convex; smooth surface; opaque white; and good growth.
(5) Litmus Milk: No change in color and no solidification or liquefaction observed.
(6) Methylred (MR) Test: Positive.
(7) Voges-Proskauer (VP) Test: Positive.
(8) Indole Formation: None.
(9) Hydrogen Sulfide Formation: None.
(10) Amylolyzability: None.
(11) Citric Acid Ulilization: Positive in Khozer Christense reaction.
(12) Inorganic Nitrogen Source Utilization: Nitrate utilized but ammonium salts not utilized.
(13) Pigment-producing-Ability: None.
(14) Urease Reaction: Negative.
(15) Oxidase Reaction: Negative.
(16) Catalase Reaction: Positive.

(17) Growth Range: pH 5~9; temperatures 20° C.~40° C.; optimum growing temperatures 32° C.~35° C.

(18) Oxygen Requirement: Facultatively anaerobic.

(19) Sugar Utilization

Acid Formation (+): D-glucose, D-fructose, D-mannose, sucrose, and glycerin.

Acid/Gas Formation (−): D-galactose, D-xylose, L-arabinose, maltose, lactose, trehalose, D-sorbitol, inositol, and starch.

(20) Salt Resistance: Salt-resistant (capable of growth in 10%~20% saline solution).

(21) Lipase Activity: Present.

(22) Lecithinase Activity: Present.

(23) Coagulase Activity: Present.

(24) Phosphatase Activity: Absent.

(25) Deoxyribonuclease Activity: Present.

This microorganism, *Staphylococcus capitis* T-1-1(SAM 0001) has been deposited with the Fermentation Research Institute Agency of Industrial Science and Technology, Ministry of International Trade and Industry at 1-1-3 Yatabe-cho Higashi, Tsukuba-gun, Ibaraki-ken, Japan as FERM P-7723. Note, this microrganism was transfered under international deposition under the Budapest Treaty on July 11, 1985 as FERM BP-834.

In practicing the process of the present invention, the lipase-producing strain of *Staphylococcus capitis* is cultured in a medium. Any arbitrary medium in which this microorganism is able to grow well may be used for the culturing. As carbon sources, glucose, sucrose, molasses, fats or oils, and the like may be used singly or in combination. As nitrogen sources, various peptones, soybean meal, corn steep liquor, yeast extract, and the like may be used singly or in combination. Salts such as $Mg^{2+}$, $Ca^{2+}$, and $Na^+$, various vitamins, and antifoaming agents may be added to the medium as needed.

Although either a culturing in liquid or on solid may be employed in the process of the present invention, an aerobic culturing in liquid is usually preferred. Aerobic conditions may be achieved by culturing with shaking or by culturing with aeration and agitation. Culturing conditions in the present invention vary with the strain and medium composition used, and the conditions which are most suitable for the intended product, i.e., lipase, are selected. Of the strains which may be used in the process of the present invention, the strain T-1-1 is cultured preferably at 20° C.~40° C., more preferably at 30° C.~37° C., and preferably at pH 5~9, more preferably at pH 6~7, resulting in satisfactory lipase production. Where the lipase-producing microorganism belonging to *Staphylococcus capitis* is cultured to prepare the novel lipase in accordance with the present invention, the productivity thereof is markedly increased by the addition to the medium of fats or oils such as olive oil or the like, or phospholipid such as lecithin or the like. Appropriate amounts of these lipids added are preferably from 0.01% to 2% of the medium. Although the period of culturing varies with the strain used, the production of lipase is completed in one to three days.

Recovery and Purification of Lipase

Since the novel lipase of the present invention is produced extra-cellularly, the broth containing lipase can be readily separated from the cells by conventional centrifugation or filtration. For further purification, the conventional techniques used for recovery and purification of enzymes, such as salting-out with ammonium sulfate, solvent precipitation, isolectric precipitation, physical adsorption with activated charcoal, calcium phosphate or the like, ion-exchange chromatography, gel filtration, or affinity chromatography, may be used singly or in combination to obtain enzyme products having different purities to meet different purposes.

An illustrative embodiment of the purification method is described as follows: A clear enzyme solution is obtained by filtration or centrifugation of the cultured broth obtained by the process of the present invention. This enzyme solution is concentrated, dialyzed in a 20 mM Tris-Hcl buffer (pH 7.0), the dialyzed concentrated solution is adsorbed on DEAE-cellulose equilibrated with the same buffer, and the adsorbed material gradient-eluted with NaCl. The present lipase is eluted with NaCl to between 0.4 M to 0.5 M. After properly concentrating the eluate, an electrophoretically homogeneous product is obtained by gel filtration using Ultragel AcA34 (manufactured by LKB) equilibrated with a 100 mM Tris-HCl buffer containing 100 mM NaCl. Alternatively, the cultured broth is concentrated using an ultrafiltration membrane, the concentrated solution brought to pH 3.9~4.0 with dilute sulfuric acid, maintained at a low temperature (preferably 4° C.) for several hours, the precipitate recovered by centrifugation or filtration, and freeze-dried to obtain an enzyme product.

Properties of the Lipase

Properties of the lipase thus purified are as follows:

(1) Substrate Specificity

A wide variety of fats or oils are hydrolyzed, for example, vegetable oils such as olive oil, coconut oil, and castor oil, animal fats and oils such as beef tallow and the like, and water-soluble lipids such as tributylene and the like.

Figure 2:
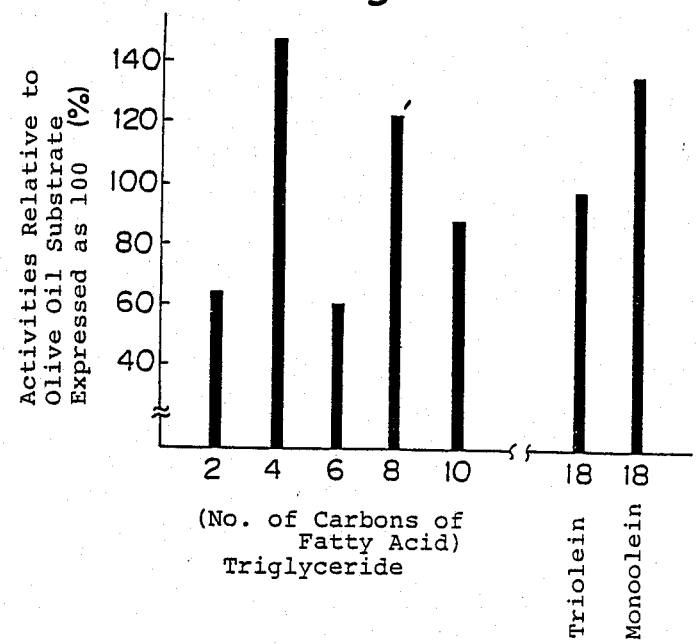
FIG. 2 shows the activities of the lipase of the present invention for different substrates relative to its activity for triolein as a substrate, expressed as 100%.

The lipase activities of the enzyme determined by using a variety of fats or oils are shown in FIG. 1 as the activities relative to those determined using olive oil as a substrate (expressed as 100%) and the activities of this lipase determined by using a variety of glycerides are shown in FIG. 2 as the activities relative to those determined by using triolein as a substrate (expressed as 100%).

(2) Optimum and Stable pH Range

Figure 3:
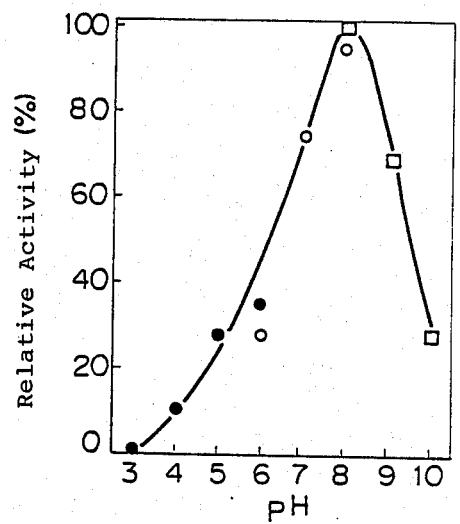
FIG. 3 shows the effects of pH on the lipase of the present invention, wherein -●- represents the activity determined by using an 0.1M acetate buffer, -o- represents the activity determined by using an 0.1M phosphate buffer, and -□- represents the activity determined by using an 0.1M glycine-NaOH buffer.

As shown in FIG. 3, the present lipase exhibits an activity within the pH range of 4.5~10.5 with the optimum pH being within the 7.5~8.0 range, which is on the weak alkali side.

Figure 4:
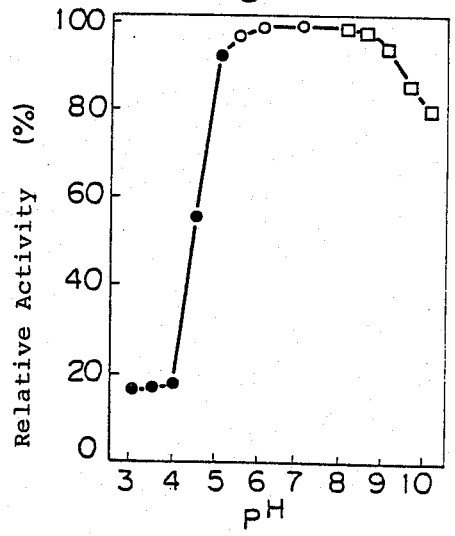
FIG. 4 shows the stability of the lipase of the present invention to pH wherein the signs used are as the same as those used in FIG. 3.

The residual lipase activities determined after having been maintained in various buffers at 4° C. for 24 hours are shown in FIG. 4. This enzyme is inactivated on the acid side below pH 4 and on the alkali side beyond pH 11. The stability thereof is maintained within the range of pH 5~pH 10.

(3) Optimum and Stable Temperature Range

Figure 5:
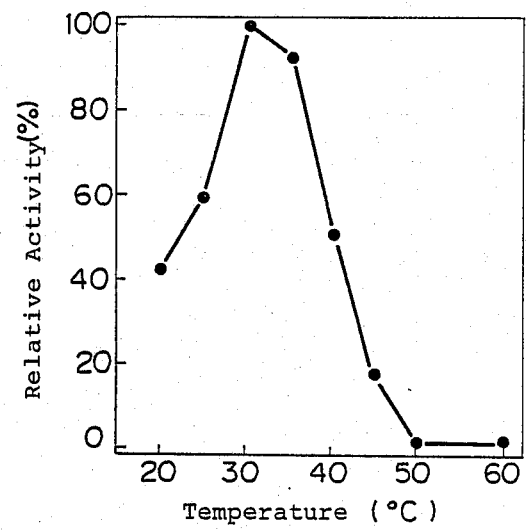
FIG. 5 shows the effects of temperatures on the activity of the lipase of the present invention.

As shown in FIG. 5, this enzyme exhibits an activity within the temperature range of 20° C.~45° C., with the optimum temperatures being within the range of 30°~35° C.

Figure 6:
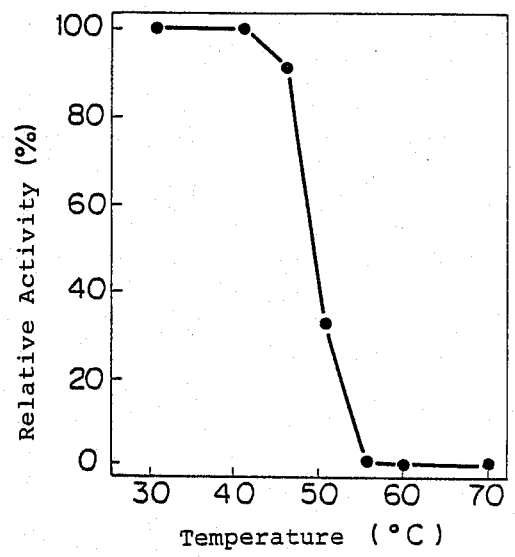
FIG. 6 shows the stabilities of the lipase of the present invention to temperatures.

The residual lipase activities determined by treatments at different temperatures are shown in FIG. 6. The residual lipase is stable at temperatures up to 45° C. when treated for 30 minutes.

(4) Inhibition and Activation

The effects of the divalent metal ions, SH reagent and surface-active agents on the lipase activity were evaluated by measuring the residual activities after treatment. No inhibition was observed with 10 mM $Ca^{2+}$, $Mn^{2+}$, $Mg^{2+}$, $Cu^{2+}$ and $Zn^{2+}$, and 1 mM $Fe^{2+}$. The lipase activity is increased 3-fold to 5-fold by the presence of $Ca^{2+}$.

The lipase activity is more than 90% inhibited by 2 mM sodium laurylsulfate (SDS), 2 mM iodine acetamide, 0.1% Tween 20, 0.1% Tween 80, and 0.1% Triton X-100.

(5) Molecular Weight

The molecular weight obtained by SDS-polyacrylamide gel electrophoresis and by gel filtration is about 128,000.

(6) Isoelectric Point

The isoelectric point determined by isoelectric focusing using Carrier-Ampholine (manufactured by LKB) is 3.9±0.1.

(7) Amino Acid Composition

The amino acid composition is given in the following table.

| Amino Acid | Mol Ratio | Number of Residues |
| --- | --- | --- |
| Asp | 13.3 | 155 |
| Thr | 6.6 | 77 |
| Ser | 8.0 | 93 |
| Glu | 12.5 | 146 |
| Gly | 7.5 | 88 |
| Ala | 7.3 | 85 |
| Val | 8.2 | 96 |
| Met | 1.8 | 21 |
| Ile | 7.7 | 90 |
| Leu | 4.6 | 54 |
| Tyr | 1.1 | 13 |
| Phe | 4.8 | 56 |
| Lys | 11.6 | 135 |
| His | 1.2 | 14 |
| Arg | 1.5 | 17 |
| Pro | 2.0 | 23 |
| ½ Cys | 0.4 | 5 |
| Trp | 1.1 | 2 |

(8) Lipoproteinlipase Activity

The present enzyme possesses lipase activity as well as lipoproteinlipase activity.

Procedure for the Determination of Lipase Activity

The procedure for the determination of lipase activity is as follows:

One milliliter of olive oil is added to a test tube ($\phi 25 \times 200$ mm) containing 5 ml of a reaction mixture consisting of 25 mM of a Tris-HCl buffer (pH 8.0) and 10 mM of $CaCl_2$, the tube is stirred vigorously with a mixer, and 0.5 ml of an enzyme solution is added to the tube. The reaction is carried out during which the tube is shaken at 300 rpm on a reciprocating shaker. The reaction is stopped on the addition of 20 ml of ethanol and the fatty acids formed are titrated with 0.05 N of an aqueous sodium hydroxide solution. The control values are likewise determined by titrating the solution obtained by first adding ethanol to a reaction mixture of the composition and then adding an enzyme solution to the same. According to a proposal by Enzyme Nomenclature; recommendations (1978) of the nomenclature committee of the International Union of Biochemistry (I.U.B.), Academic Press, a unit of lipase activity is defined as that amount of lipase required to liberate 1 $\mu$mole of fatty acids per minute under reaction conditions.

The following examples are provided solely for further illustration:

EXAMPLE 1

A liquid medium (pH 7.0) comprising 0.1% glucose, 0.5% yeast extract, 1% Polypeptone (peptone manufactured by Takeda Pharmaceutical Industry Ltd.) and 0.5% NaCl was inoculated with *Staphylococcus capitis* T-1-1 (FERM P-7723) and incubated for 18 hours at 30° C. with shaking to obtain an inoculum. One hundred milliliters of a liquid medium (pH 6.3) comprising 10% AFF peptone (a soybean protein hydrolysate manufactured by Ajinomoto Co.) and 0.5% NaCl was distributed to a Sakaguchi flasks (500 ml) and was sterilized. The medium was inoculated with 1% by volume of the inoculum and the inoculated medium was incubated for 2 days at 30° C. with shaking at 300 rpm.

The cultured broth was collected, the bacterial cells removed by centrifugation, and a supernatant solution was obtained, which assayed 10.3 U/ml in lipase activity. One thousand three hundred sixty milliliters of the enzyme solution was subjected to salting out with ammonium sulfate, the resulting precipitating fraction collected by centrifugation, dialyzed overnight in 20 mM Tris-HCl buffer (pH 7.0), chromatographed using a DEAE-cellulose column (manufactured by Whatman; $\phi 36 \times 210$ mm) equilibrated with the same buffer, and gradient elutions were carried out with NaCl at molar concentrations ranging from 0 to 1. The present lipase was eluted with NaCl between 0.4M and 0.5M. The active fraction was suitably concentrated, the concentrated solution was re-chromatographed using an Ultrogel AcA34 column (manufactured by LKB; $\phi 25 \times 440$ mm) equilibrated with 100 mM Tris-HCl buffer (pH 8.0)/100 mM NaCl, and an electrophoretically homogeneous enzyme product was obtained. The specific activity (activity per milligram of protein) after the purification process was 136.2 U/mg with a yield of 34%.

EXAMPLE 2

The supernatant solution obtained by the same method as that described in Example 1 was concentrated by ultrafiltration (with a Pellicon Labocassette obtained from Millipore (Japan) Ltd.; 10,000-molecular weight ultrafilter membrane PTGC OLC 05), the concentrated solution chromatographed using a DEAE-cellulose column equilibrated with 20 mM Tris-HCl buffer (pH 7.0), and an electrophoretically homogeneous enzyme product was obtained by the purification method described in Example 1.

EXAMPLE 3

Seven liters of a liquid medium (pH 6.3) comprising 5% AFF peptone and 0.5% NaCl was introduced into a 14-liter jar fermenter (manufactured by New Brunswick Scientific Inc.) and sterilized. The medium was inoculated with 200 ml of an inoculum culture of *Staphylococcus capitis* T-1-1 (FERM P-7723)) obtained as described in Example 1, and culturing was carried out for 24 hours at 30° C. with agitation at 300 rpm and aeration at 2.0 v.v.m. The cultured broth was centrifuged to remove the cells and the supernatant solution concentrated 4-fold by ultrafiltration (a Pellicon Labocassette from Millipor (Japan) Ltd.; 10,000-molecular weight ultrafilter membrane PTGC OLC 05). The concentrated solution was adjusted to pH 3.9 with hydrochloric acid and was allowed to stand at a low temperature (preferably at 4° C.) for two hours. The precipitate was recovered by centrifugation or filtration and dissolved, and the solution was freeze-dried to obtain a purified enzyme product. The specific activity (activity per milligram of protein) after the purification process was 87.0 U/mg, with a yield of 28%.

EXAMPLE 4

Ten microliters of triolein (having a 99% purity and manufactured by Nakarai Chemical) serving as a substrate was added to 2 ml of a buffer comprising 25 mM Tris-HCl buffer (pH 8.0) containing 10 mM $CaCl_2$. To this was added the enzyme preparation obtained as described in Example 1 so that the total enzyme activity reach 3U, and the reaction was carried out at 30° C. Similar reactions were also conducted using commercially available lipases respectively derived from *Rhizopus arrhizus*, *Candida cylindracea*, and *Pseudomonas* sp. for comparison. One hundred microliters each of samples were taken during the reactions at 10, 30, 60, and 120 minutes, the reaction products extracted with 100 $\mu l$ of chloroform, and 1 $\mu l$ portions of the extract were assayed by silica gel thin-layer chromatography for identification of the reaction products.

The system of this thin-layer chromatography was as follows:

Solvent System: Chloroform/Acetone (96:4).

Color Development: 1% $Ce(SO_4)_2$/10% $H_2SO_4$, heating.

Thin-layer Plate: Silica gel Kieselgel 60F$_{254}$ (manufactured by Merck & Co.).

Figure 7:
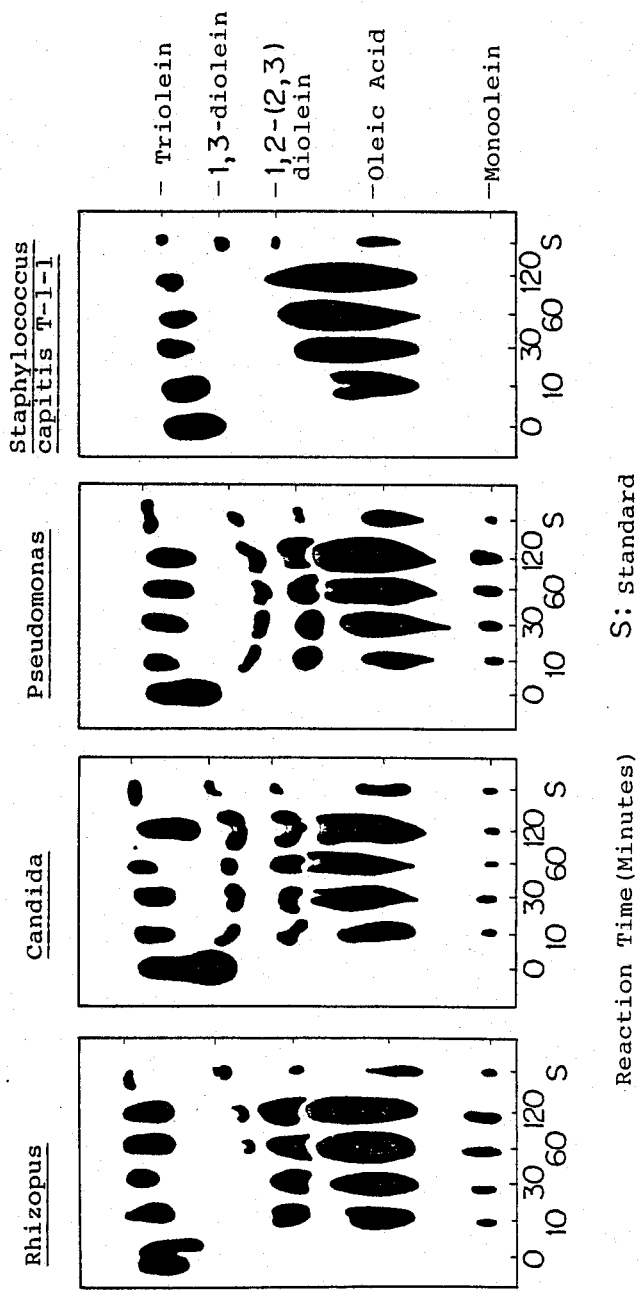
FIG. 7 shows thin-layer chromatograms comparing the lipase of the present invention and that of the prior art with respect to the reaction product.

The results are shown in FIG. 7. As can be seen from this figure, where lipases respectively derived from Rhizopus (fungi), Candida (yeast), and Pseudomonas (bacteria) were used, 1,3-diolein and 1,2-(2,3)-diolein, which are diglycerides, as well as monoolein, which is a monoglyceride, were produced at all sampling time intervals during the reactions and these products even showed a tendency to increase with the passage of reaction time. Whereas when the lipase of the present invention was used, monoolein and diolein were not detected throughout the reaction period, with oleic acid being the only substance produced.

EXAMPLE 5

Figure 8:
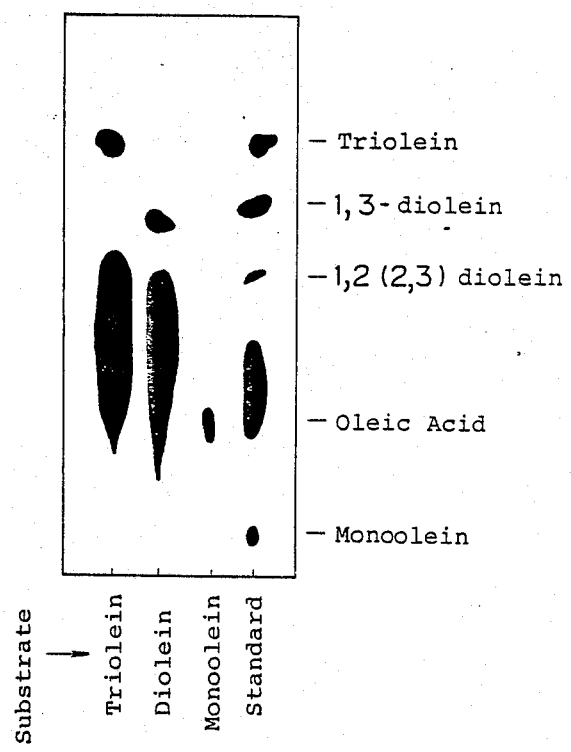
FIG. 8 is a thin-layer chromatogram showing activities of the lipase of the present invention to different glyceryl oleates; and, FIGS. 9 and 10 are thin-layer chromatograms showing the products resulting from hydrolysis of triolein with different enzyme solutions (from different strains) of the present invention.

Enzyme reactions were carried out using triolein, diolein, and monoolein as substrates for the enzyme preparation obtained as described in Example 1 and the reaction products were identified by silica-gel thin-layer chromatography. In these identification tests 7.5 $\mu l$ of triolein (99% in purity), 5 $\mu l$ of diolein (99% in purity), and 3 $\mu l$ of monoolein (99% in purity) were added respectively to three reaction mixtures each consisting of 1 ml of 25 mM Tris-HCl buffer (pH 8.0)/10 mM $CaCl_2$, and to each reaction mixture was added an enzyme solution to bring the total activity to 3 U. Reactions were then carried out for 60 minutes at 30° C., the reaction products extracted with chloroform, and the extracts subjected to silica-gel thin-layer chromatograph as in Example 4. The results are shown in FIG. 8, which definitely shows that only oleic acid was produced from any one of the substrates.

EXAMPLE 6

One percent olive oil was added to each of the media containing 10% AFF peptone (See Example 1) and the media which had been respectively inoculated with the following strains of *Staphylococcus capitis* were incubated for 3 days at 30° C. with shaking:

(1) *Staphylococcus (St.) capitis* ATCC 27840
(2) St. capitis ATCC 27841
(3) St. capitis ATCC 27842
(4) St. capitis ATCC 27843
(5) St. capitis FERM P7723 (FERM BP-834)

After culturing, the cultured broth was centrifuged to remove the cells and the supernatant solution was used as an enzyme solution. The lipase activities of the enzyme solutions were as follows:

| No. | Strain | Lipase Activity (U/ml) |
|---|---|---|
| 1 | *Staphylococcus capitis* ATCC 27840 | 11.7 |
| 2 | *Staphylococcus capitis* ATCC 27841 | 13.5 |
| 3 | *Staphylococcus capitis* ATCC 27842 | 4.6 |
| 4 | *Staphylococcus capitis* ATCC 27843 | 12.6 |
| 5 | *Staphylococcus capitis* T-1-1 | 6.1 |

Figure 9:
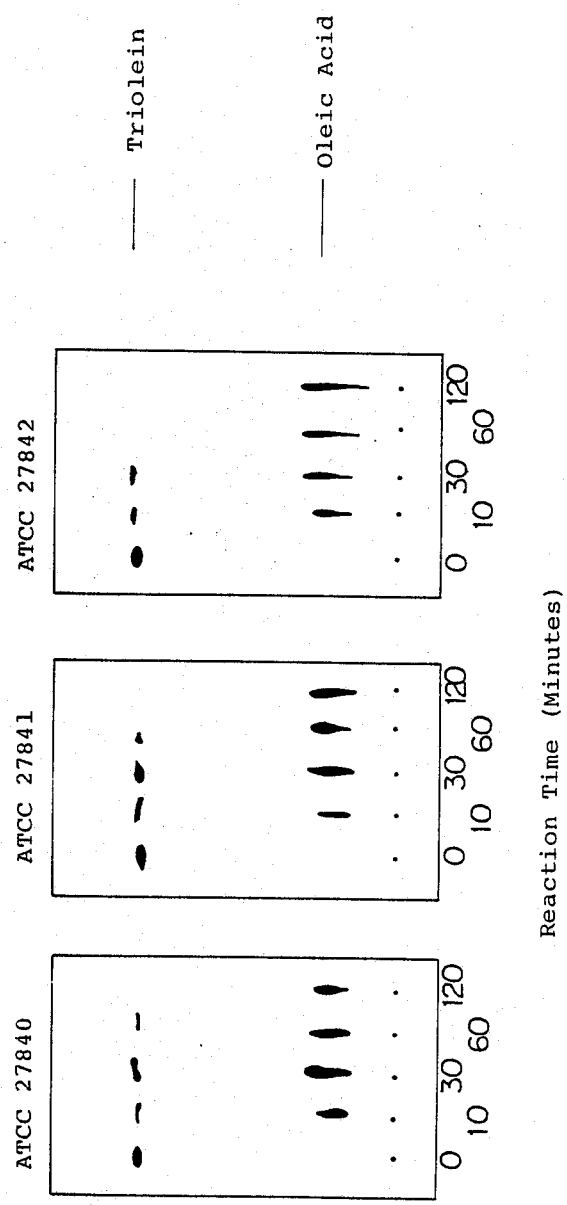
Figure 10:
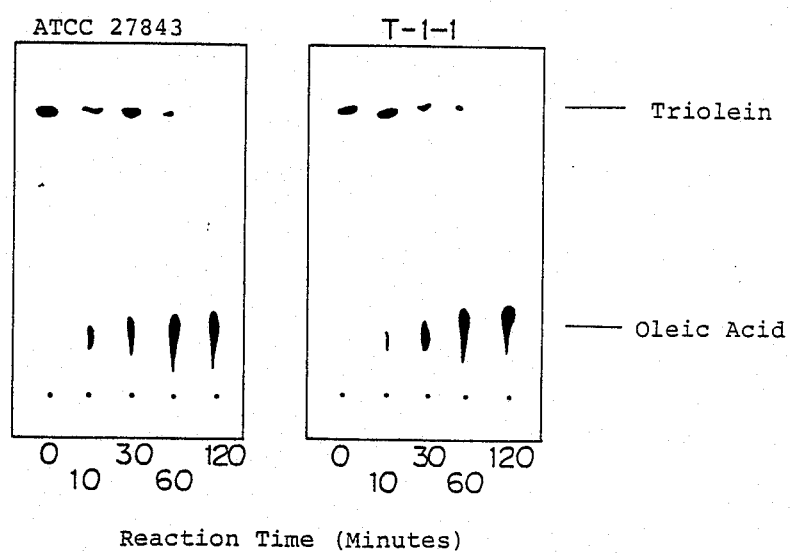

The enzyme solution was diluted with Tris-HCl buffer (pH 8.0)/10 mM $CaCl_2$ to bring the lipase activity to 3 U/ml and to 1 ml of the diluted solution was added 10 $\mu l/ml$ of triolein. The mixture was shaken at 30° C. and 100-microliter samples were taken at 0, 10, 30, 60, and 120 minutes. The samples were then extracted with 100 $\mu l$ of chloroform and 2 $\mu l$ portions of the chloroform layer were subjected to thin-layer chromatography as described in Example 3. The results are shown in FIG. 9. As seen from FIG. 9, monoolein and diolein were not detected in the reaction solutions which contained enzyme solutions derived from one of the different strains.

CAPABILITY OF EXPLOITATION IN INDUSTRY

This invention is useful for the preparation on an industrial scale of lipase which, in effect, completely hydrolyzes triglyceride to fatty acids and glycerin and, in turn, this lipase is useful for the economic preparation of fatty acids, by the hydrolysis of fats or oils.

We claim:

1. A process for producing a novel lipase comprising the steps of culturing *Staphylococcus capitis* T-1-1 (SAM 001) FERM BP-384 in a culture medium to accumulate the lipase in the culture broth and recovering the lipase from the broth.

2. The process of claim 1 wherein said lipase has an optimum activity under slightly alkaline conditions and is capable of substantially completely converting triglycerides into fatty acids and glycerine.

* * * * *